United States Patent [19]
Chen

[11] Patent Number: 6,053,957
[45] Date of Patent: Apr. 25, 2000

[54] WASTE TREATMENT PROCESS AND DEVICE THEREOF

[75] Inventor: Thomas Chen, Cerritos, Calif.

[73] Assignee: ATT Environmental Technology Inc., Cypress, Calif.

[21] Appl. No.: 09/121,410

[22] Filed: Jul. 24, 1998

[51] Int. Cl.[7] .................................. C02F 1/02; C02F 1/22; C05F 9/00
[52] U.S. Cl. .................. 71/11; 241/23; 241/DIG. 38; 422/23; 422/32; 588/220; 588/228; 53/127
[58] Field of Search ................ 241/23, DIG. 37, 241/DIG. 38; 422/24, 32, 110, 193, 292, 307, 309; 588/220, 227, 228; 53/127; 210/188, 218; 428/524; 100/92; 110/346; 71/11, 12, 14, 15

[56] References Cited

U.S. PATENT DOCUMENTS

| | | | |
|---|---|---|---|
| 2,146,902 | 2/1939 | Martin | 44/27 |
| 3,524,417 | 8/1970 | Stone | 110/8 |
| 3,864,840 | 2/1975 | Baskin | 34/5 |
| 3,884,162 | 5/1975 | Schuster | 110/8 R |
| 3,902,435 | 9/1975 | Schuster | 110/7 R |
| 3,985,086 | 10/1976 | De Tola | 110/8 P |
| 4,355,521 | 10/1982 | Tsai | 62/196 B |
| 5,337,581 | 8/1994 | Lott | 62/264 |
| 5,614,107 | 3/1997 | Mallia, Jr. | 210/771 |

*Primary Examiner*—Steven P. Griffin
*Assistant Examiner*—Elin Warn
*Attorney, Agent, or Firm*—Raymond Y. Chan; David and Raymond

[57] ABSTRACT

The present invention provides a waste treatment process and device thereof which can reduce the size and weight of organic waste by decomposing the waste to powder form and bacteria free substance that may be used as a kind of fertilizer for plants. The waste is first frozen by liquefied nitrogen in a cooling chamber to a temperature less than −200° F., wherein during this freezing procedure, the gas generated from the waste must be removed from the cooling chamber. Then, the frozen nitrogen is immediately transferred to a heated chamber having a temperature of at least 160° F. but not exceed 200° F. During this heating procedure, the water content of the waste is sucked out of the heated chamber, so that the waste is decomposed to form the bacteria free powder.

20 Claims, 4 Drawing Sheets

WASTE TREATMENT PROCESS AND DEVICE THEREOF

FIELD OF THE PRESENT INVENTION

The present invention relates to waste treatment, and more particularly to a waste treatment process and device thereof, capable of reducing the size and even the weight of the waste by decomposing the waste, such as garbage, rubbish, refuse, and the like, to powder form and bacteria free substance that may be used as a kind of fertilizer for plants.

BACKGROUND OF THE PRESENT INVENTION

Human beings create civilization as well as garbage. From industries to families, tons of wastes are produced everyday and everywhere. The waste treatment becomes a common headache to every government. Organic waste would produce bacteria and poison gas that are harmful to human health. Plastic waste made of polyvinyl chloride, foam rubber and the like requires hundreds of years to decompose. Burying, combustion and recycling are the most common waste treatment methods. However, burying occupies a large area of land. Combustion generates air pollution. Recycling still needs a lot of man efforts and the relative economic benefit is low.

The major object of the waste-combustion treatment is to reduce the weight and size of all kinds of the waste, so that the burying field may handle more waste. In fact, it is a self-deceiving matter that results in serious air pollution. According to the law of "Conservation of Matter", the mass of the waste will not be eliminated after combustion. The weight and size of the waste seems to be reduced during combustion just because the waste combusts and reacts with fuel and oxygen to form smoke including various kinds of gas and chemical particles discharged in the air. These gas and chemical particles are more difficult to control that the discharged gas will dissipate in the air and the chemical particles will finally fall back to the ground everywhere. In other words, although the waste-combustion treatment burns the waste to ash, the loss of weight still exists in the earth in form of generated gases and chemical particles.

Especially, the grease in organic waste is the biggest headache of the waste-combustion treatment. It is well known that when organic waste is combusted, poison gas and matters are generated to seriously pollute the earth. Therefore, we must carefully exclude the organic waste before the waste is processed with combustion treatment in order to reduce the poison pollution. It is another costly task to do.

Moreover, the chemical treatment before combustion for eliminating smell and neutralizing poison matters requires the addition of respective chemicals. Such additives are also conservated even after combustion that, in fact, become additional waste to the environment.

Besides, the best that a waste producer can do is to pack the waste with different garbage bags according to the nature of waste. We can do very little in reducing the size of the waste produced everyday. Transportation is the first expensive headache to every government. Although the personal computer successfully enters each family and enterprise, we can't find any personal waste treatment device available in market, which is adapted to be installed at home or in the factory for taking care of our own garbage, industrial waste, rubbish, and refuse. It would be a great idea to have a personal waste treatment device that can reduce up to approximately 90% of the size of the waste. It would further be a remarkable concept to decompose the waste to powder form and bacteria free substance so as to reduce it size instead of the conventional combustion treatment. It is not a dream but a respectful duty of human being to the earth.

SUMMARY OF THE PRESENT INVENTION

It is thus a first object of the present invention to provide a waste treatment process, which can reduce the size as well as the weight of the waste by decomposing the waste, such as garbage, rubbish, refuse, and the like, to powder form and bacteria free substance that may be used as a kind of fertilizer for plants.

A further object of the present invention is to provide a waste treatment device which is specifically adapted for installing at home and in the factory so that everyone can pre-treat their own garbage, rubbish, refuse, and industrial waste easily and efficiently.

Another object of the present invention is to provide a waste treatment process and device thereof, which is specifically adapted to reduce both the size and weight of the organic waste without smoke discharging to the air.

Yet another object of the present invention is to provide a waste treatment process and device thereof, wherein the treatment operation is easy, fast and safe.

Still another object of the present invention is to provide a waste treatment process and device thereof, which is suitable for the government to utilize in the public waste treatment plant so as to minimize the treatment cost and possible pollution.

In order to accomplish the above objects, the present invention provides a waste treatment process which comprises the steps of:

(a) sealedly enclosing a predetermined amount of waste in a cooling chamber;

(b) rapidly freezing the waste to at least −200° F. by spraying a predetermined amount of liquefied nitrogen around the waste inside the cooling chamber for a predetermined period of time;

(c) exhausting all kinds of gas generated around the frozen waste inside the sealed cooling chamber and sending the exhausted gas to a filter unit after depressurizing, wherein the gas is rapidly sucked out from the cooling chamber due to the pressure and temperature difference between the freezing temperature and high pressure inside the cooling chamber and the outside temperature and atmosphere pressure;

(d) filtering the gas sucked from the cooling chamber by the filter unit for ensuring no harmful gas would be output;

(e) immediately transferring the frozen waste into a heated chamber having a temperature of at least 160° F. for a predetermined period of time;

(f) decomposing the frozen waste in the heated chamber to form a bacteria free powder substance due to an instantaneous temperature difference of at least 400° F. between the frozen waste and the heated chamber;

(g) dehydrating water content of the waste in the heated chamber and removing the water content out of the heated chamber so as to accelerating the decomposition of the waste; and (h) clearing the dehydrated powder substance from the heated chamber.

The above waste treatment process is processed by means of a waste treatment device, which comprises:

a housing divided into an upper cooling chamber and a lower heated chamber, wherein the cooling chamber has a gas outlet valve provided thereon and the heated chamber has a water outlet provided thereon;

a partition wall installed between the cooling chamber and the heated chamber so as to entirely isolate the cooling chamber and the heated chamber from heat conduction therebetween;

an openable cover door sealedly installed to the cooling chamber, wherein the surrounding walls of the cooling chamber, the partition wall and the cover door defines a sealed receiving room for receiving a predetermined amount of waste therein;

an injector, which is firmly installed on the cover door and connected to a liquefied nitrogen source, having an emitting head extended inside the cooling chamber for injecting the liquefied nitrogen around the waste inside the cooling chamber for freezing the waste to at least −200° F.;

a control means for ensuring the injector to spray liquefied nitrogen into the cooling chamber from the liquefied nitrogen source only when the cover door entirely and sealedly shuts off the cooling chamber;

a filter unit for filtering gas generated around the waste when the liquefied nitrogen is sprayed to freeze the waste inside the cooling chamber, wherein the gas is sucked through the gas outlet valve and sent to the filter unit after depressurizing;

an actuating means for driving the partition wall to open after the waste inside the cooling chamber is frozen by the liquefied nitrogen emitted from the emitting head of the injector, wherein when the frozen waste moves to the heated chamber, the actuating means drives the partition wall back to its isolating position to entirely isolate the cooling chamber and the heated chamber from heat conduction;

a heat source for maintaining the heated chamber at a temperature of at least 160° F., wherein when the frozen waste is moved from the cooling chamber to the heated chamber, the frozen waste inside the heated chamber is decomposed to form a powder substance due to an instantaneous temperature difference of at least 400° F. between the frozen waste and the heated chamber; and a water exhaust means for removing the water content of the waste from the heated chamber so as to accelerating the decomposition of the waste in the heated chamber.

DETAILED DESCRIPTION OF THE PREFERRED EMBODIMENT

Figure 1:
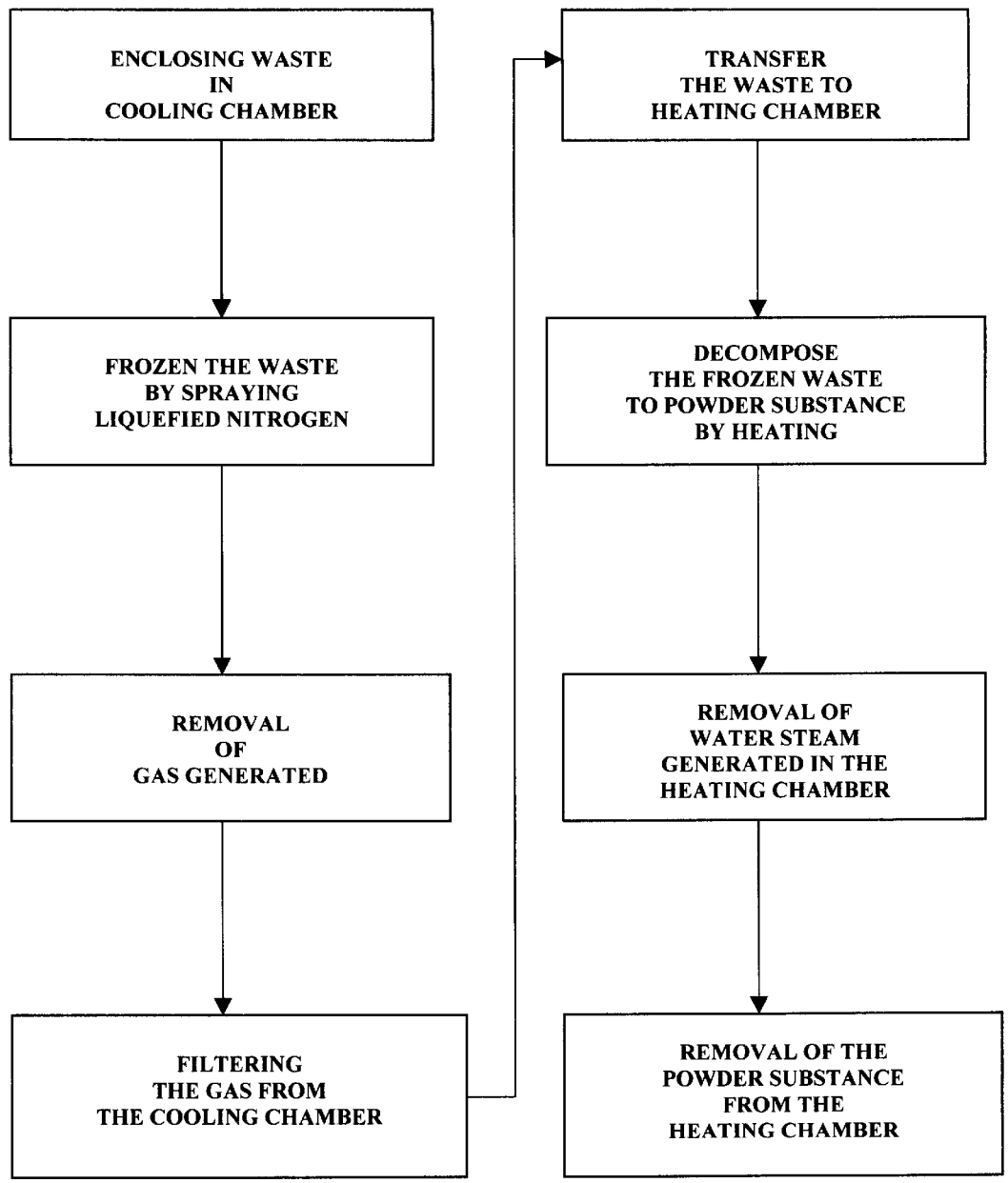
FIG. 1 is a block diagram of a waste treatment process in accordance with the present invention.

Referring to FIG. 1 of the drawings, the present invention provides a smokeless waste treatment process, wherein no combustion is involved. The waste treatment process of the present invention can reduce size of the waste and even the weight of the organic waste by decomposing the waste, such as garbage, rubbish, refuse, and the like, to powder form and bacteria free substance that may be used as a kind of fertilizer for planting. The waste treatment process comprises the following steps.

Step A: Sealedly enclose a predetermined amount of waste in a cooling chamber. The cooling chamber should be insulated from outside. The more waste to be treated the bigger the cooling chamber is required.

Step B: Rapidly freeze the waste to at least −200° F. by spraying a predetermined amount of liquefied nitrogen around the waste inside the cooling chamber for a predetermined period of time.

Liquefied nitrogen is commonly used in frozen food industry because liquefied nitrogen is capable of freezing any object to very low temperature rapidly. Therefore, when the liquefied nitrogen is sprayed around the waste inside the sealed cooling chamber until, preferably, all surfaces of the waste are contacted with the liquefied nitrogen, the waste matter will be entirely frozen within a relatively short period. The liquefied nitrogen will permeate into the waste and render the waste matter becoming brittle. Generally, the more waste to be frozen the more liquefied nitrogen is required to inject into the cooling chamber. According to the present invention, it is preferable to spray the liquefied nitrogen, as even as possible, around the waste inside the sealed and insulated cooling chamber for 4 to 6 minutes or more, depending on the amount and nature of the waste to be treated, until all the waste in the cooling chamber is preferably frozen to −230° F. to −270° F. so as to ensure all the frozen waste can be fragmentary.

Step C: Exhaust all kinds of gas generated around the frozen waste inside the sealed cooling chamber and send the exhausted gas to a filter unit after depressurizing, wherein the gas will be rapidly sucked out from the cooling chamber due to the pressure and temperature difference between the freezing temperature and high pressure inside the cooling chamber and the outside temperature and atmosphere pressure.

Due to the fact that waste gas and even poison gas may be generated from the frozen waste during the above freezing step B, especially for the organic waste, those waste gas and poison gas must be removed from the cooling chamber. Therefore, a gas outlet valve can be provided on the cooling chamber. During the above freezing step B or before the above freezing step B is completed, the gas outlet valve is opened for one time or several times for approximately 15 to 30 seconds each time. Then, all kinds of gas, including oxygen gas, in the cooling chamber will be automatically sucked from the cooling chamber through the gas outlet valve due to the pressure and temperature difference between the higher outside temperature and atmosphere pressure outside the cooling chamber and the very low temperature and high pressure inside the cooling chamber. During this gas exhausting step C, about 10% of water vapor of the frozen waste will be exhausted also.

Step D: Filter the gas sucked from the cooling chamber by the filter unit for ensuring no harmful gas would be output.

In order to avoid the waste gas and poison gas directly pollute the environment, it is preferred to force all the gas sucked from the cooling chamber inputting in the filter unit so as to purify the gas by removing all poison and harmful chemicals thereof before it is released to the atmosphere. It should be notified that, in order to avoid unwanted damages to the filter unit, the compressed gas exhausted from the cooling chamber is preferably depressurized by reducing its compressed pressure to atmospheric pressure before entering the filter unit.

Step E: Immediately transfer the frozen waste into a heated chamber having a temperature of at least 160° F. for a predetermined period of time, wherein the heated chamber is a sealed chamber insulated from outside. The frozen waste must be transferred from the cooling chamber to the heated chamber rapidly. In other words, the frozen waste is preferred to remain at the low temperature, −230° F. to −270° F., while it is transferred into the heated chamber.

Step F: Decompose the frozen waste in the heated chamber to form a bacteria free powder substance due to an instantaneous temperature difference of at least 400° F. between the frozen waste and the heated chamber.

According to the present invention, the heated chamber is preferred to be maintained at 170° F. to 190° F. but not exceed 200° F. for at least 2.5 minutes. Practically, the heated chamber is preferred to be pre-heated and kept such high temperature range when the frozen waste is transferred inside the heated chamber.

The frozen waste in the heated chamber will be decomposed to powder form and generate water steam when it is treated with a rapid temperature difference as much as 400° F. to 460° F., from the freezing temperature (−230° F. to −270° F.) in the cooling chamber to the hot temperature (170° F. to 190° F.) in the heated chamber. It is worth to mention that if the temperature change gradually, the molecules of the waste will not decompose. However, when the frozen waste is suddenly treated in a heated environment to experience such an instantaneous temperature difference, all the molecules of the waste will be decomposed instantly.

Step G: Dehydrate water content of the heating waste in the heated chamber and remove the water content out of the heated chamber. When the heating waste is almost absolutely dehydrated, a bacteria free powder substance is achieved in the heated chamber.

According to the present invention, the water steam generated from the heating waste and the water content of the waste can be removed from heated chamber by sucking through a water outlet provided on the heated chamber. This dehydrating step G can also accelerate and enhance the decomposition of the waste. The water content sucked from the heated chamber can be further filtered and collected in a water tank.

Since most organic matter contains as much as 90% of water, if the water content is removed from the organic matter, the size and weight of the matter will be largely reduced. Accordingly, the volume and weight of the dehydrated powder substance are minimized in comparison with the waste before treated. Moreover, the bacteria contained in the waste will also be decomposed too.

Step H: Clear the dehydrated powder substance from the heated chamber.

In view of the above disclosed process, the waste can be decomposed to the bacteria free powder substance within a relatively short period of time. In view of the organic waste, the size and waste of the powder substance formed can be reduced to approximately 10% the waste before treated. According to the present invention, the total treatment time is as less as 7 to 10 minutes only. Since the highest temperature involved in the instant waste treatment process does not exceed 200° F., no waste will be burnt inside the heated chamber. In other words, no combustion is involved in the present invention, so that no smoke will be provided. Air pollution caused by the conventional combustion treatment is avoided. Moreover, the grayish powder substance produced does not occupy space during transportation and can even be used as a fertilizer for planting. It can be proud to say that, after the waste treatment process of the present invention, the waste is not a waste any more.

The efficiency of the waste treatment process of the present invention can be further enhanced by compressing and crashing the waste to be treated into small pieces before placing in the cooling chamber in the above step A, so that the cooling chamber can receive and freeze more waste each time.

The waste treatment process of the present invention, step A to step H, can also be utilized for processing animal and human dead bodies. The present innovative process is fast, economic and clean.

Figure 2:
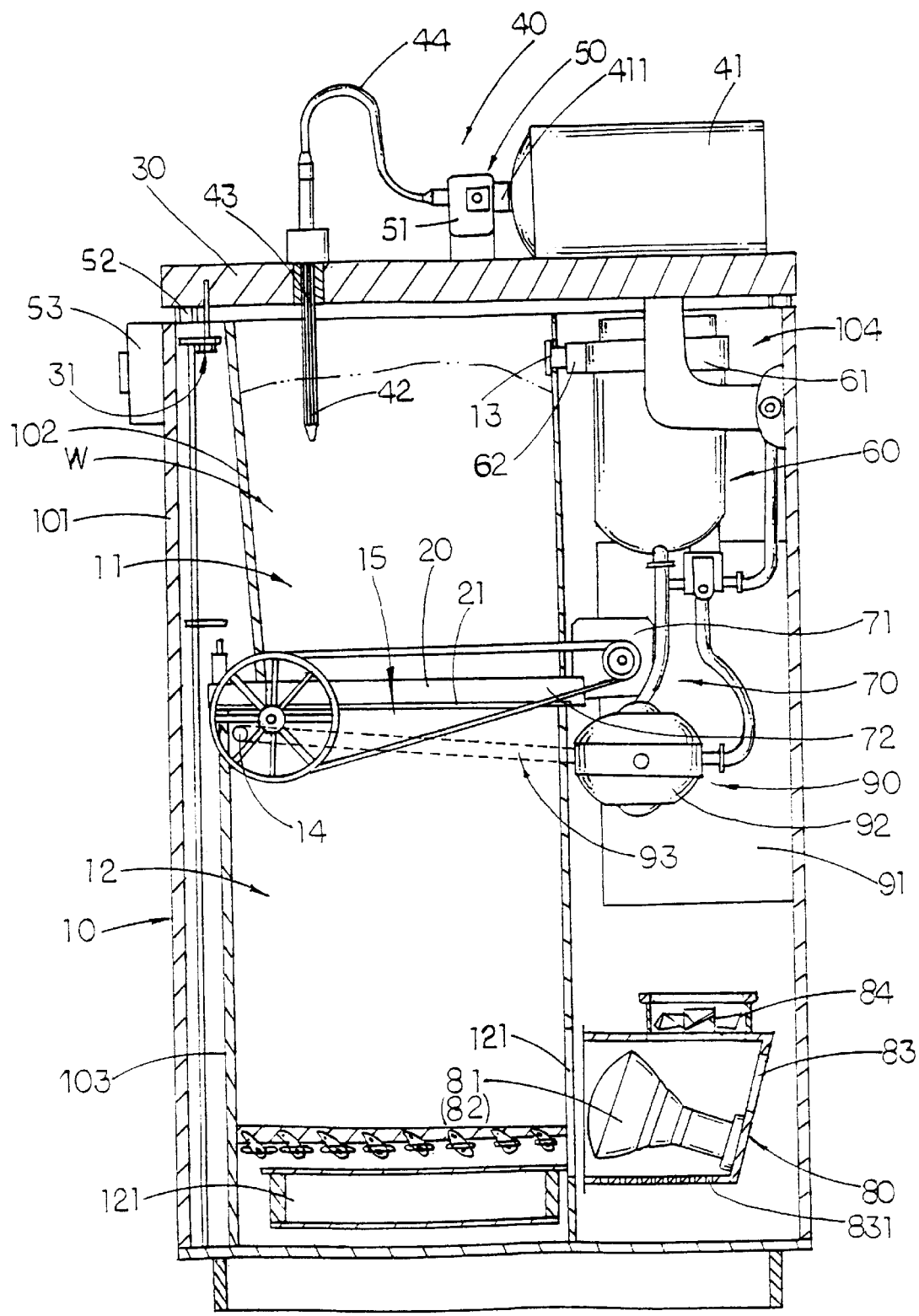
FIG. 2 is a sectional front view of a waste treatment device in accordance with a preferred embodiment of the present invention.
Figure 3:
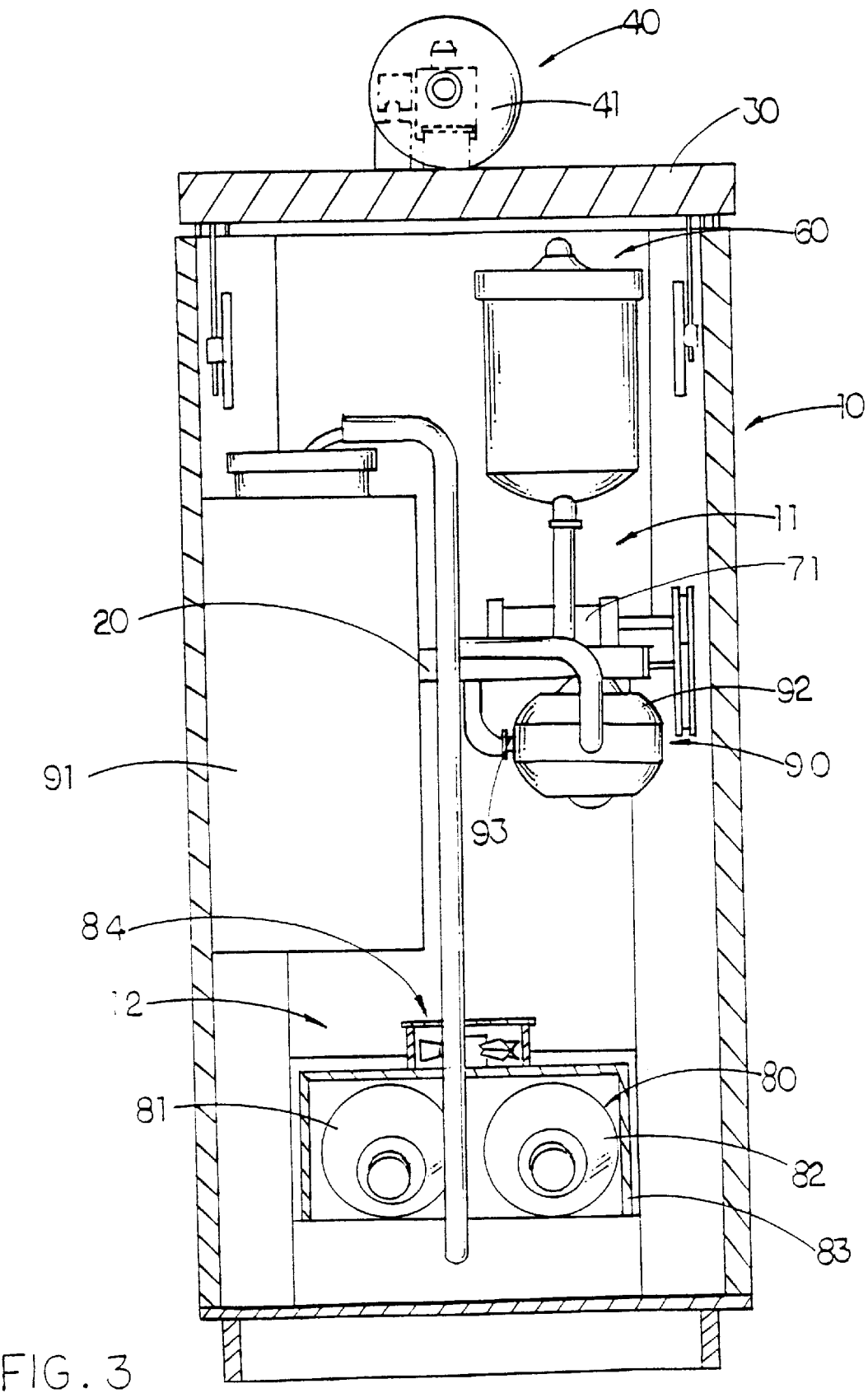
FIG. 3 is a sectional side view of the waste treatment device in accordance with the above preferred embodiment of the present invention.
Figure 4:
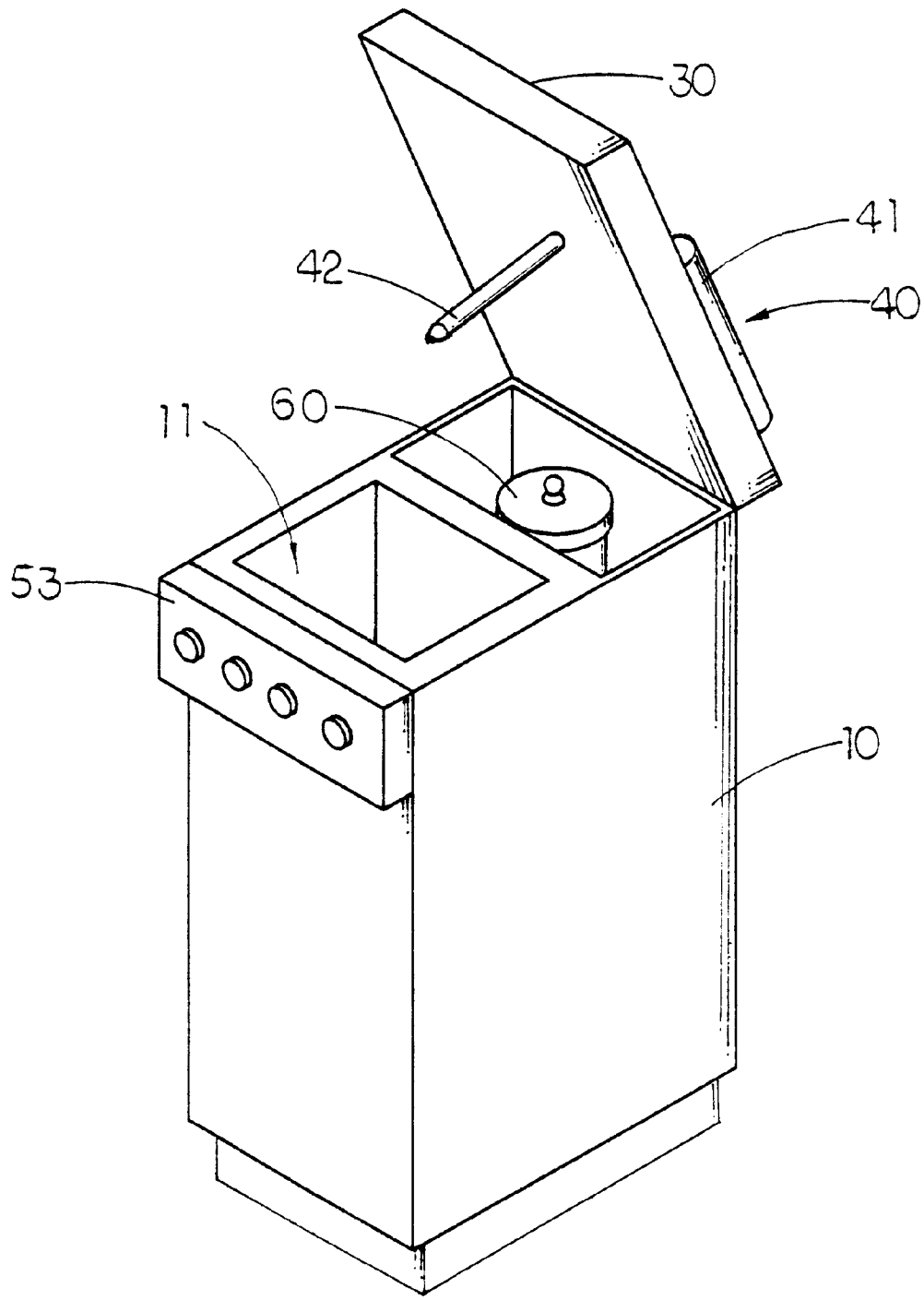
FIG. 4 is a perspective view of the waste treatment device with the cover door opened in accordance with the above preferred embodiment of the present invention.

Referring to FIGS. 2 to 4, a waste treatment device specifically designed for processing the waste treatment process disclosed above is illustrated. The device has a relatively small size adapted to install in house or factory to handle the owner's daily waste. The waste treatment device according to a preferred embodiment of the present invention comprises a housing 10, a partition wall 20, an openable cover door 30, an injector 40, a control means 50, a filter unit 60, an actuating means 70, a heat source 80, and a water exhaust means 90.

The housing 10 is divided into an upper cooling chamber 11 and a lower heated chamber 12 thereunder, wherein the cooling chamber 11 has a gas outlet valve 13 provided thereon and the heated chamber 12 has a water outlet 14 provided thereon. As shown in FIG. 2, the housing 10 comprises an exterior case 101, a first tank 102 mounted on an upper position inside the exterior case 101 to define the cooling chamber 11 therein, a second tank 103 mounted on a lower position inside the exterior case 101 to define the heated chamber 12 therein. Both the first tank 102 and the second tank 103 are made of heat insulation material, wherein the first tank 102 must able to resist a low temperature up to −270° F. and the second tank 103 must able to resist a high temperature up to 200° F.

The gas outlet valve 13 is provided on a side wall of the first tank 102. A passage opening 15 is formed between the cooling chamber 11 and the heated chamber 12. The partition wall 20 is disposed between the first tank 102 and the second tank 103 to normally cover the passage opening 15. A chamber insulator layer 16 is provided between the adjacent sides of the first and second tanks 102, 103 to prevent heat conduction between the cooling chamber 11 and the heated chamber 12. The exterior case 101 also divides a control room 104 for installing the filter unit 60, the actuating means 70, the heat source 80, and the water exhaust means 90 therein. A removable tray 121 is disposed on a bottom of the heated chamber 12.

As shown in FIG. 2, the partition wall 20 which is filled with insulation material is hingedly installed between the cooling chamber 11 and the heated chamber 12 so as to entirely isolate the cooling chamber 11 and the heated chamber 12 from heat conduction therebetween. According to the preferred embodiment, the partition wall 20 has one side hinged to a side wall of the second tank 103, so that when the partition wall 20 is driven to swing downwards, the passage opening 15 between the cooling chamber 11 and the heated chamber 12 is opened. Normally, the partition wall 20 is remained horizontally to cover the passage opening 15. A gasket 21 is affixed on top of the partition wall 20 so as to ensure no clearance occurred at the passage opening 15 when the partition wall 20 is horizontally closed.

As shown in FIGS. 2 to 4, the openable cover door 30 is sealedly installed on top of the cooling chamber 11, wherein the surrounding walls of the cooling chamber 11, the partition wall 20 and the cover door 30 defines a sealed receiving room for receiving a predetermined amount of waste W therein. The cover door 30 which is filled with insulation material is hingedly connected to a rear side of the exterior case 101, so that the cover door 30 can be swung upwardly, as shown in FIG. 4, to open the cooling chamber 11 for inputting the waste W into the cooling chamber 11. When the cooling chamber 11 is functioning, the cover door 30 must be remained closed and locked to prevent any accidentally open operation thereof The injector 40, which is firmly installed on the cover door 30 and connected to a liquefied nitrogen source 41, having an emitting head 42 extended inside the cooling chamber 11. The liquefied nitrogen source 41 is a liquefied nitrogen tank firmly mounted on a rear portion of the cover door 30. The liquefied nitrogen tank 41 has a normally closed exit valve 411 provided at a front end thereof to insure no liquefied nitrogen will be escaped without opening the exit valve 411. The injector 40 comprises an injecting tube 43 sealedly extended through the cover door 30, and a delivery tube 44 sealedly connected between a top end of the injecting tube 43 and the control means 50, wherein the emitting head 42 is provided at a bottom end of the injecting tube 43 for spraying out the liquefied nitrogen.

It is worth to mention that the amount of the liquefied nitrogen to be injected into the cooling chamber 11 depends on the size of the cooling chamber 11, i.e. the volume of the waste to be treated. For example, if the cooling chamber 11 has a size of 12"×13"×12" or 7.5 gallon, the preferable amount of the liquefied nitrogen to be injected into the cooling chamber 11 is 40 to 60 c.c. in order to ensure all the waste is totally frozen to the predetermined temperature of −200° F. to −270° F.

As shown in FIGS. 2 and 4, the control means 50 is installed on the cover door 30 for ensuring the injector 40 to spray liquefied nitrogen into the cooling chamber 11 from the liquefied nitrogen source 41 only when the cover door 30 entirely and sealedly shuts off the cooling chamber 11. The control means 50 comprises a solenoid valve 51 connected between the delivery tube 44 and the exit valve 411 for opening the exit valve 411 of the liquefied nitrogen tank 41 when it is activated, a door sensor 52 for detecting whether the cover door 30 is closed or opened, and a control panel 53 mounted on the cover door 30 or any desired position on the exterior case 101 for the user to operate the waste treatment device. When the door sensor 52 detects that the cover door 30 is in opened condition, the solenoid valve 51 will be ineffective even the user activates the solenoid valve 51 to open the exit valve 411 of the liquefied nitrogen tank 41 through the control panel 53 so as to ensure safety.

The cover door 30 further comprises a lock means 31 for locking the closed cover door 30 when it is entirely pushed down. During operation, when the user closes the cover door 30, the door sensor 52 can determine whether the cover door 30 fully closes the cooling chamber 11. Then, the user must entirely actuate the lock means 31 to lock the closed cover door 30. After that, the user may operate the control panel 53 to activate the solenoid valve 51 to open the exit valve 411 of the liquefied nitrogen tank 41, so that liquefied nitrogen would output from the liquefied nitrogen tank 41 to the injector 40, wherein the liquefied nitrogen is injected into the cooling chamber 11 via the injecting tube 43 and the delivery tube 44. Either the user fails to fully close the cover door 30, or the partition wall 20 fails to entirely closed, or the cover door 30 fails to be locked properly, the solenoid valve 51 is ineffective and the exit valve 411 will remain close, and thus no liquefied nitrogen inside the liquefied nitrogen tank 41 will be supplied.

The filter unit 60 comprises at least a filtering element such as activated carbon, a depressurizer 61 provided thereon, and a transmitting gas duct 62 connecting the gas outlet valve 13 of the cooling chamber 11 with the depressurizer 61 of the filter unit 60, so that when the liquefied nitrogen is sprayed around the waste inside the cooling chamber 11, the gas generated around the waste is sucked through the gas outlet valve 13 to the filter unit 60 via the transmitting gas duct 62 and the compressed gas exhausted from the cooling chamber is preferably depressurized by reducing its compressed pressure to atmospheric pressure by the depressurizer 61 to atmospheric pressure before entering the filter unit 60. The filter unit 60 then filters all the poison and harmfwl chemicals in the gas. The purified gas is then transferred to a water tank 91 installed inside the control room 104 or directly released to the air.

As shown in FIG. 2, the actuating means 70 which is installed inside the control room 104 for driving the partition wall 20 to open after the waste W inside the cooling chamber 11 is frozen by the liquefied nitrogen emitted from the emitting head 42 of the injector 40, wherein when the frozen waste W falls to the heated chamber 12, the actuating means 70 drives the partition wall 20 back to its closing position to entirely isolate the cooling chamber 11 and the heated chamber 12 from heat conduction.

The actuating means 70, according to the present embodiment, comprises a two-way motor 71 and a transmission unit 72 connected to the partition wall 20. The power output from the motor 71 is transmitted through the transmission unit 72 to drive the partition wall 20 swinging down and up. The power transmission can be carried by gears or metal chain. The motor 71 is automatically activated by timer control. The user can preset the cooling time of the waste W in the cooling chamber 11 on the control panel 53, i.e. the time period of injecting the liquefied nitrogen into the cooling chamber 11. After the spraying of the liquefied nitrogen into the cooling chamber 11 stops, the gas outlet valve 13 is activated to close and the motor 71 of the actuating means 70 is activated to output power to drive the partition wall 20 to swing downwards in order to open the passage opening 15. Therefore, the frozen waste W would fall to the removable tray 121 inside the heated chamber 12 due to gravity, and then the motor 71 is activated to rotate in opposite direction for driving the partition wall 20 to swing back upwardly to absolutely re-close the passage opening 15 between the cooling chamber 11 and the heated chamber 12.

As shown in FIGS. 2 and 3, the heat source 80 is installed inside the control room 104 for heating and maintaining the heated chamber 12 within a predetermined temperature range, preferably 170° F. to 190° F., so that when the frozen waste W having a freezing temperature of preferably −230° F. to −270° F. is suddenly moved into the heated chamber, the waste W will be decomposed inside the heated chamber 12 to form a powder substance due to an instantaneous temperature difference of about 400° F. between the frozen waste W and the hot environment in the heated chamber 12.

The heat source 80 comprises a pair of heaters 81, 82 which are UV or IR lamps mounted within a lamp box 83 with a plurality of ventilating holes 831 provided thereon for enhancing ventilation, wherein the two heaters 81, 82 are positioned close to a heating window 122 on the heated chamber 12 so as to transfer heat into the heated chamber 12 through the heating window 122 for maintaining the predetermined hot temperature inside the heated chamber 12 between 170° F. to 190° F.

The heat source 80 further comprises a dissipating fan 84 installed above the lamp box 83 so as to help the residual heat in the lamp box 83 to dissipate outside the exterior case 10.

As shown in FIGS. 2 and 3, the water exhaust means 90 is installed inside the control room 104 for removing the water steam, which is generated during the decomposing of the waste W, from the heated chamber 12.

The water exhaust means 90 comprises the water tank 91, a water exhaust pump 92 and a water conduit 93 connecting the water exhaust pump 92 with the water outlet 14 on the heated chamber 12 and the water tank 91. Therefore, during the decomposing of the waste W, the water exhaust pump 92 is activated simultaneously to suck the water steam generated from the heating waste W and the water content of the heating waste W inside the heated chamber 12 to the water tank 91 through the water outlet 14. After the waste W is decomposed to the powder substance which is collected in the removable tray 121, the user can simply take out the removable tray 121 from the heated chamber 12.

The size and power of the waste treatment device varies according to different situations. It can be built as large as a waste treatment plant. For home use, the device can be made in more compact size as shown in FIGS. 2 to 4. Since the entire operation time is as short as several minutes only, the user may treat his or her produced garbage right away. The operation of the waste treatment device is so simple. The user merely needs to open the cover door 30 and place the waste inside the cooling chamber 11. Then, the user can simply close the cover door 30 and activate the device on the control panel 53. The device will process the waste automatically step by step. As mentioned above, if the cover door 30 is not sealedly closed in position, the whole waste treatment device can not be activated and is not in function so as to ensure safety.

For industry usage, the waste treatment device is made in larger size in order to handle more waste at one time. The waste treatment device of the present invention can be installed in the garbage collecting truck too, so that the truck can immediately decompose the collected waste in order to avoid bad smell and bacteria growth before burying. Moreover, the truck can transport more amount of waste than usual.

In view of above, the waste treatment process and device of the present invention can substantially achieve the following advantages:

(1) It can reduce the weight and size of the waste by decomposing the waste, such as garbage, rubbish, refuse, and the like, to powder form and bacteria free substance that may be used as a kind of fertilizer for plant.

(2) It is specifically adapted for installing at home and in the factory so that everyone can handle their own garbage, rubbish, refuse, and industrial waste easily and efficiently.

(3) It is specifically adapted to reduce both the size and weight of the organic waste without smoke discharging to the air.

(4) The treatment operation is easy, fast and safe.

(5) It is especially suitable for the government to utilize in the public waste treatment plant so as to minimize the treatment cost and possible pollution.

(6) Since the waste treatment process is specifically adapted to decompose the organic waste, it can also provide remarkable efficiency when the device of present invention is made in relative large size and applied to the waste treatment plant for handling organic waste such as the greasy kitchen waste, the family waste, and even the animal corpses.

What is claimed is:

1. A waste treatment process, comprising the steps of:
   (a) sealedly enclosing an amount of waste in a cooling chamber;
   (b) spraying liquefied nitrogen around said waste inside said cooling chamber for a predetermined period of time until said amount of waste is rapidly frozen to a freezing temperature of at least −200° F.;
   (c) exhausting all kinds of gas generated around said frozen waste inside said sealed cooling chamber to a filter unit;
   (d) filtering said gas exhausted from said cooling chamber by said filter unit for ensuring no harmful gas is output;
   (e) immediately transferring said waste into a heated chamber having a temperature not to exceed 200° F. for a period of time;
   (f) decomposing said frozen waste in said heated chamber to form a bacteria free powder substance due to an instantaneous temperature difference of at least 400° F. between said frozen waste and said heated chamber;
   (g) dehydrating water content of said waste in the said heated chamber removing said water content out of said heated chamber so as to accelerate the decomposition of said waste; and
   (h) clearing said dehydrated powder substance from said heated chamber.

2. A waste treatment process, as recited in claim 1, wherein, in step (b), said liquefied nitrogen is sprayed evenly around said waste inside said sealed and insulated cooling chamber for 4 to 6 minutes and said waste is preferred to be frozen to −230° F. to −270° F.

3. A waste treatment process, as recited in claim 2, wherein, in step (c), a gas outlet valve is provided on said cooling chamber, therefore before said freezing step (b) completes, said gas outlet valve is opened for 15 to 30 seconds, and then said gas in said cooling chamber is automatically sucked from said cooling chamber through said gas outlet valve due to a high pressure and temperature difference between said cooling chamber and outside, and that, after depressurizing to atmospheric pressure, said exhausted gas from said cooling chamber is sent to said filter unit.

4. A waste treatment process, as recited in claim 3, wherein, in step (e), while said frozen waste is transferred into said heated chamber, said frozen waste is preferred to remain at −230° F. to −270° F.

5. A waste treatment process, as recited in claim 4, wherein, in step (f), said frozen waste in said heated chamber is preferred to be heated not to exceed 200° F. for at least 2.5 minutes.

6. A waste treatment process, as recited in claim 5, wherein, in step (g), said water content is removed from said heated chamber by sucking through a water outlet provided on said heated chamber.

7. A waste treatment device, comprising:
   a housing having an upper cooling chamber and a lower heated chamber thereunder, wherein said cooling chamber has a gas outlet valve provided thereon and said heated chamber has a water outlet provided thereon;
   a partition wall installed between said cooling chamber and said heated chamber so as to entirely insulate said cooling chamber and said heated chamber from heat conduction therebetween;

an openable cover door sealedly installed to said cooling chamber, wherein said surrounding walls of said cooling chamber, said partition wall and said cover door defines a sealed receiving room for receiving a amount of waste therein;

an injector, which is firmly installed on said cover door and connected to a liquefied nitrogen source, having an emitting head extended inside said cooling chamber for injecting said liquefied nitrogen around said waste inside said cooling chamber for freezing said waste to at least −200° F;

a control means for ensuring said injector to spray liquefied nitrogen into said cooling chamber from said liquefied nitrogen source only when said cover door entirely and sealedly shuts off said cooling chamber;

a filter unit for filtering gas generated around said waste when said liquefied nitrogen is sprayed around said waste inside said cooling chamber, wherein said gas is exhausted through said gas outlet valve and sent to said filter unit after depressurizing;

an actuating means for driving said partition wall to open after said waste inside said cooling chamber is frozen by said liquefied nitrogen emitted from said emitting head of said injector, wherein when said frozen waste falls to said heated chamber, said actuating means drives said partition wall back to its isolating position to entirely isolate said cooling chamber and said heated chamber from heat conduction;

a heat source for maintaining said heated chamber at a temperature not to exceed 200° F., wherein when said frozen waste is moved from said cooling chamber to said heated chamber, said frozen waste inside said heated chamber is decomposed to form a powder substance due to an instantaneous temperature difference of at least 400° F. between said frozen waste and said heated chamber; and a water exhaust means for removing water content of said waste from said heated chamber so as to accelerate the decomposition of said waste in said heated chamber and reduce the size and weight of said waste.

8. A waste treatment device, as recited in claim 7, wherein a passage opening is formed between said cooling chamber and said heated chamber, said partition wall normally covering said passage opening.

9. A waste treatment device, as recited in claim 8, wherein said housing also divides a control room for installing said filter unit, said actuating means, said heat source, and said water exhaust means therein.

10. A waste treatment device, as recited in claim 9, wherein said partition wall has one side hinged to a side wall of said heated chamber, and that when said partition wall is driven to swing downwards, said passage opening between said cooling chamber and said heated chamber is opened.

11. A waste treatment device, as recited in claim 10, wherein a gasket is affixed on top of said partition wall so as to ensure no clearance occurred at said passage opening when said partition wall is closed.

12. A waste treatment device, as recited in claim 11, wherein said cover door is sealedly installed on top of said cooling chamber and is filled with insulation material, said cover door being hingedly connected to a rear side of housing, so that said cover door is capable of swinging upwardly to open said cooling chamber for inputting said waste into said cooling chamber, wherein when said liquefied nitrogen is spraying inside said cooling chamber, said cover door must be remained closed and locked.

13. A waste treatment device, as recited in claim 12, wherein said liquefied nitrogen source comprises a liquefied nitrogen tank firmly mounted on a rear portion of said cover door, said liquefied nitrogen tank having a normally closed exit valve provided at a front end thereof, and that said injector comprises an injecting tube sealedly extended through said cover door and a delivery tube sealedly connected between a top end of said injecting tube and said control means, wherein said emitting head is provided at a bottom end of said injecting tube for spraying out said liquefied nitrogen.

14. A waste treatment device, as recited in claim 13, wherein said control means, which is installed on said cover door, comprises a solenoid valve connected between said delivery tube and said exit valve for opening said exit valve of said liquefied nitrogen tank when it is activated, a door sensor for detecting whether said cover door is closed or opened, and a control panel mounted on said housing for operating said waste treatment device, wherein when said door sensor detects that said cover door is in opened condition, said solenoid valve is ineffective even when said solenoid valve is activated to open said exit valve of said liquefied nitrogen tank through said control panel.

15. A waste treatment device, as recited in claim 14, wherein said cover door further comprises a lock bar for locking said closed cover door.

16. A waste treatment device, as recited in claim 14, wherein said filter unit which comprises at least a filtering element, a depressurizer provided thereon, and a transmitting gas duct connecting said gas outlet valve of said cooling chamber with said depressurizer of the filter unit, so that when said liquefied nitrogen is sprayed around said waste inside said cooling chamber, said gas generated around said waste is sucked through said gas outlet valve to said filter unit via said transmitting gas duct and said gas exhausted from said cooling chamber is depressurized by reducing to atmospheric pressure before entering said filter unit, wherein said filter unit filters all poison and harmful chemicals in said gas.

17. A waste treatment device, as recited in claim 16, wherein said actuating means comprises a two-way motor and a transmission unit connected to said partition wall, in which a power output from said motor is transmitted through said transmission unit to drive said partition wall swinging down and up.

18. A waste treatment device, as recited in claim 17, wherein said heat source comprises at least a heater which is a UV or IR lamp mounted within a lamp box with a plurality of ventilating holes provided thereon for enhancing ventilation, wherein said heater is positioned close to a heating window provided on said heated chamber so as to transfer heat into said heated chamber through said heating window for maintaining said temperature of said heated chamber, and that said heat source further comprises a dissipating fan installed above said lamp box so as to help a residual heat in said lamp box to dissipate outside said housing.

19. A waste treatment device, as recited in claim 18, wherein said water exhaust means comprises a water tank, a water exhaust pump and a water conduit connecting said water exhaust pump with said water outlet on said heated chamber and said water tank, therefore, during decomposing of said waste, said water exhaust pump is activated simultaneously to suck steam generated from said heating waste and said water content of said heating waste inside said heated chamber to said water tank through said water outlet, and that said powder substance is collected in a removable tray disposed inside said heated chamber.

20. A waste treatment device, as recited in claim 19, wherein said housing comprises an exterior case, a first tank mounted on an upper position inside said exterior case to define said cooling chamber therein, a second tank mounted on a lower position inside said exterior case to define said heated chamber therein, in which both said first tank and said second tank are made of heat insulation material, moreover a chamber insulator layer is provided between said adjacent sides of said first and second tanks to prevent heat conduction between said cooling chamber and said heated chamber.

* * * * *